(12) United States Patent
Norsten et al.

(10) Patent No.: US 7,645,558 B2
(45) Date of Patent: *Jan. 12, 2010

(54) INKLESS REIMAGEABLE PRINTING PAPER AND METHOD

(75) Inventors: Tyler B. Norsten, Oakville (CA); Gabriel Iftime, Mississauga (CA); Peter M. Kazmaier, Mississauga (CA); Barkev Koshkerian, Thornhill (CA); Naveen Chopra, Oakville (CA)

(73) Assignee: Xerox Corporation, Norwalk, CT (US)

( * ) Notice: Subject to any disclaimer, the term of this patent is extended or adjusted under 35 U.S.C. 154(b) by 180 days.

This patent is subject to a terminal disclaimer.

(21) Appl. No.: 11/762,177

(22) Filed: Jun. 13, 2007

(65) Prior Publication Data
US 2008/0311494 A1    Dec. 18, 2008

(51) Int. Cl.
G03F 7/00 (2006.01)
G03F 7/004 (2006.01)

(52) U.S. Cl. ............... 430/270.1; 430/19; 430/270.15; 430/945; 430/962

(58) Field of Classification Search .............. 430/270.1, 430/19, 270.15, 945, 962
See application file for complete search history.

(56) References Cited

U.S. PATENT DOCUMENTS

| | | | |
|---|---|---|---|
| 3,825,427 A | 7/1974 | Inoue et al. | |
| 3,877,941 A | 4/1975 | Lohmann | |
| 3,961,948 A | 6/1976 | Saeva | |
| 4,425,161 A | 1/1984 | Shibahashi et al. | |
| 4,598,035 A | 7/1986 | Usami et al. | |
| 4,659,649 A | 4/1987 | Dickinson et al. | |
| 4,931,337 A | 6/1990 | Miyazaki et al. | |
| 5,124,236 A | 6/1992 | Yamaguchi et al. | |
| 5,262,280 A | 11/1993 | Knudsen et al. | |
| 5,376,511 A | 12/1994 | Tatezono et al. | |
| 5,458,874 A | 10/1995 | Pereira et al. | |
| 5,677,107 A | 10/1997 | Neckers | |
| 5,691,100 A | 11/1997 | Kudo et al. | |
| 5,691,395 A | 11/1997 | Knudsen et al. | |
| 5,747,225 A | 5/1998 | Manico et al. | |
| 6,067,185 A | 5/2000 | Albert et al. | |
| 6,103,378 A | 8/2000 | Yao et al. | |
| 6,200,646 B1 | 3/2001 | Neckers et al. | |
| 6,528,221 B2 | 3/2003 | Takezawa et al. | |

(Continued)

FOREIGN PATENT DOCUMENTS

CA    2 053 094 A1    4/1992

(Continued)

OTHER PUBLICATIONS

M. Irie, "Diarylethense for Memories and Switches," Chem Reviews, 100, pp. 1685-1716 (2000).

(Continued)

*Primary Examiner*—Amanda C. Walke
(74) *Attorney, Agent, or Firm*—Oliff & Berridge, PLC (57) ABSTRACT

An image forming medium includes a paper substrate and an imaging layer coated on or impregnated into a paper substrate, where the imaging layer is formed of an imaging composition that includes an alkoxy substituted diarylethene photochromic material dissolved or dispersed in a solvent or polymeric binder, and where the imaging composition exhibits a reversible transition between a colorless and a colored state.

28 Claims, 2 Drawing Sheets

U.S. PATENT DOCUMENTS

| | | | |
|---|---|---|---|
| 6,579,662 | B1 | 6/2003 | Zheng et al. |
| 6,680,281 | B2 | 1/2004 | Tajiri et al. |
| 6,761,758 | B2 | 7/2004 | Boils-Boissier et al. |
| 6,866,981 | B2 | 3/2005 | Furukawa et al. |
| 6,867,408 | B1 | 3/2005 | Gu et al. |
| 6,906,118 | B2 | 6/2005 | Goodbrand et al. |
| 7,018,714 | B2 | 3/2006 | Kobayashi et al. |
| 7,057,054 | B2 | 6/2006 | Irie |
| 7,205,088 | B2 | 4/2007 | Iftime et al. |
| 7,214,456 | B2 | 5/2007 | Iftime et al. |
| 7,229,740 | B2 | 6/2007 | Iftime et al. |
| 7,256,921 | B2 | 8/2007 | Kumar et al. |
| 7,332,257 | B2 | 2/2008 | Miyako et al. |
| 7,381,506 | B2 | 6/2008 | Iftime et al. |
| 7,441,887 | B2 | 10/2008 | Senga et al. |
| 2002/0160318 | A1 | 10/2002 | Richter et al. |
| 2003/0130456 | A1 | 7/2003 | Kim et al. |
| 2005/0012998 | A1 | 1/2005 | Kumar et al. |
| 2005/0244744 | A1 | 11/2005 | Kazmaier et al. |
| 2005/0269556 | A1 | 12/2005 | Evans et al. |
| 2006/0001944 | A1 | 1/2006 | Chopra et al. |
| 2006/0222972 | A1 | 10/2006 | Chopra et al. |
| 2006/0222973 | A1 | 10/2006 | Iftime et al. |
| 2006/0236470 | A1 | 10/2006 | Sabnis et al. |
| 2006/0251988 | A1 | 11/2006 | Iftime et al. |
| 2006/0257785 | A1 | 11/2006 | Johnson |
| 2007/0054215 | A1 | 3/2007 | Iftime et al. |
| 2007/0072110 | A1 | 3/2007 | Iftime et al. |
| 2007/0112103 | A1 | 5/2007 | Zhou et al. |

FOREIGN PATENT DOCUMENTS

| | | |
|---|---|---|
| DE | 29 06 193 A1 | 8/1980 |
| EP | 1 367 111 | 12/2003 |
| EP | 1 405 891 | 4/2004 |
| EP | 1 591 829 | 11/2005 |
| EP | 1 591 831 | 11/2005 |
| FR | 2774998 | 8/1999 |
| GB | 2 430 257 | 3/2007 |
| JP | 57-136645 | 8/1982 |
| JP | A-61-175087 | 8/1986 |
| JP | A-5-265129 | 10/1993 |
| JP | A-11-30835 | 2/1999 |
| JP | A 11-322739 | 11/1999 |
| JP | A-2000-256347 | 9/2000 |
| JP | A-2002-179672 | 6/2002 |
| JP | A-2002-240441 | 8/2002 |
| JP | A-2002-285146 | 10/2002 |
| JP | A-2003-255489 | 9/2003 |
| JP | A-2003-255490 | 9/2003 |
| JP | A-2004-039009 | 2/2004 |
| JP | A-2004-045037 | 2/2004 |
| JP | A-2004-091638 | 3/2004 |
| JP | A-2004-149501 | 5/2004 |
| JP | A-2004-256780 | 9/2004 |
| JP | A-2005-082507 | 3/2005 |
| JP | A-2005-250463 | 9/2005 |
| WO | WO 97/31033 | 8/1997 |
| WO | WO 00/16985 A1 | 3/2000 |
| WO | WO 2006/039130 A1 | 4/2006 |
| WO | WO 2007/105699 A1 | 9/2007 |
| WO | WO 2008/043853 A2 | 4/2008 |

OTHER PUBLICATIONS

Kentaro Morimitsu et al., "Dithienylethenes With a Novel Photochromic Performance," J. Org. Chem., vol. 67, pp. 4574-4578 (2002).

Kentaro Morimitsu et al., "Thermal Cycloreversion Reaction of a Photochromic Dithienylperfluorocyclopentene with tert-Butoxy Substituents at the Reactive Carbons," The Chemical Society of Japan, 2002, p. 572-573.

U.S. Appl. No. 11/762,152, filed Jun. 13, 2007, to Iftime et al.
U.S. Appl. No. 11/762,327, filed Jun. 13, 2007, to Iftime et al.
U.S. Appl. No. 11/762,147, filed Jun. 13, 2007, to Iftime et al.
U.S. Appl. No. 11/762,098, filed Jun. 13, 2007, to Iftime et al.
U.S. Appl. No. 11/762,157, filed June 13, 2007, to Iftime et al.
U.S. Appl. No. 11/762,153, filed Jun. 13, 2007, to Iftime et al.
U.S. Appl. No. 11/762,144, filed Jun. 13, 2007, to Kazmaier et al.
U.S. Appl. No. 11/762,150, filed Jun. 13, 2007, to Norsten et al.
U.S. Appl. No. 11/762,107, filed Jun. 13, 2007, to Iftime et al.
U.S. Appl. No. 11/762,176, filed Jun. 13, 2007, to Norsten et al.
U.S. Appl. No. 11/762,307, filed Jun. 13, 2007, to Norsten et al.
U.S. Appl. No. 11/762,159, filed Jun. 13, 2007, to Kazmaier et al.
U.S. Appl. No. 11/762,311, filed Jun. 13, 2007, to Kazmaier et al.

Wojtyk et al., "Effects of metal ion complexation on the spiropyran-merocyanine interconversion: development of a thermally stable photo-switch," J. Chem. Soc. Chem, Comm., pp. 1703-1704, 1998.

"Dolch Introduces World's First Ruggedized Notebook with Integrated Printer" available at http://news.thomasnet.com/fullstory/7005/447, pp. 1-4, Feb. 6, 2002.

Masamitsu Shirai et al., "Photoacid and Photobase Generators: Chemistry and Applications to Polymeric Materials," Prog. Polym. Sci. vol. 21, pp. 1-45 (1996).

T. Hirose et al., "Self-Assembly of Photochromic Diarylethenes With Amphiphilic Side Chains: Reversible Thermal and Photochemical Control," J. Org. Chem., 71, pp. 7499-7508 (2006).

T. Norsten et al., "Photoregulation of Fluorescence in a Porphyrinic Dithienylethene Photochrome," J. Am. Chem. Soc., 123(8), pp. 1784-1785 (2001).

Vladimir I. Minkin, "Photo-, Thermo-, Solvato-, and Electrochromic Spiroheterocyclic Compounds," Chemical Reviews, 104, 5, pp. 2751-2776 (2004).

Takayuki Suzuki et al., "Stabilization of the merocyanine form of photochromic compounds in fluoro alcohols is due to a hydrogen bond", Chem. Commun., 2685-2686 (1998).

Ronald F.M. Lange et al., "Supramolecular polymer interactions based on the alternating copolymer of styrene and Maleimide" Macromolecules, 28, 782-783 (1995).

Vladimir I. Minkin et al., "Perimidine spirocyclohexa dienones" in Organic Photochromic and Thermochromic Compounds, VI, Plenum Press, pp. 315-340 (1999).

John Biteau et al., "Photochromism of Spirooxazine-Doped Gels," J. Phys. Chem., 100, 9024-9031 (1996).

Leonard J. Prins et al., "Noncovalent Synthesis Using Hydrogen Bonding," Angew. Chem. Int. Ed., 40, 2382-2426 (2001).

Terry M. Cresp et al., "A Synthesis of $\alpha\beta$-Unsaturated Aldehydes," J. Chem. Soc., Perkin Trans., 1, pp. 37-41 (1974).

Elliot Berman et al., "Photochromic Spiropyrans. I. The Effect of Substituents on the Rate of Ring Closure," J. Am. Chem. Soc., 81, 5605-5608 (1959).

Sheng-Hua Liu et al., "Synthesis of Negative Photochromic Crowned Spirobenzopyrans," Syn. Commun., 30, 5, 895-902 (2000).

Yu M. Chunaev et al., "Reaction of the Fischer Base With Nitro- and Bromo-Substituted $\alpha$Hydroxycinnamaldehydes," Chem. Heterocycl. Compd., 628-631 (1984).

O.M. Babeshko et al., "Spiro-2H-Oxocines", Khimiya Geterotsiklicheskikh Soedinenii, No. 11, pp. 1490-1492, Nov. 1976.

Samir Kumar Mandal et al., "Titanocene(III) mediated radical cyclizations of epoxides for the synthesis of medium-sized cyclic ethers", Tetrahedron, vol. 63, pp. 11341-11348, 2007.

Sep. 9, 2009 European Office Action issued in European Application No. 08 155 983.3 - 1217.

FIG. 2B

INKLESS REIMAGEABLE PRINTING PAPER AND METHOD

TECHNICAL FIELD

This disclosure is generally directed to a substrate, method, and apparatus for inkless printing on reimageable paper. More particularly, in embodiments, this disclosure is directed to an inkless reimageable printing paper utilizing a composition that is imageable and eraseable by heat and light, such as comprising an alkoxy substituted dithienylethene dispersed in a solvent or polymeric binder, where the composition exhibits a reversible transition between a colorless and a colored state. Imaging is conducted by applying UV light and optional heat to the imaging material to cause a color change, and erasing is conducted by applying visible light and optionally heat to the imaging material to reverse the color change. Other embodiments are directed to inkless printing methods using the inkless printing substrates, and apparatus and systems for such printing.

CROSS-REFERENCE TO RELATED APPLICATIONS

Disclosed in commonly assigned U.S. patent application Ser. No. 11/123,163, filed May 6, 2005, is an image forming medium, comprising a polymer, a photochromic compound containing chelating groups embedded in the polymer, and a metal salt, wherein molecules of the photochromic compound are chelated by a metal ion from the metal salt.

Disclosed in commonly assigned U.S. patent application Ser. No. 10/835,518, filed Apr. 29, 2004, is an image forming method comprising: (a) providing a reimageable medium comprised of a substrate and a photochromic material, wherein the medium is capable of exhibiting a color contrast and an absence of the color contrast; (b) exposing the medium to an imaging light corresponding to a predetermined image to result in an exposed region and a non-exposed region, wherein the color contrast is present between the exposed region and the non-exposed region to allow a temporary image corresponding to the predetermined image to be visible for a visible time; (c) subjecting the temporary image to an indoor ambient condition for an image erasing time to change the color contrast to the absence of the color contrast to erase the temporary image without using an image erasure device; and (d) optionally repeating procedures (b) and (c) a number of times to result in the medium undergoing a number of additional cycles of temporary image formation and temporary image erasure.

Disclosed in commonly assigned U.S. patent application Ser. No. 10/834,722, filed Apr. 29, 2004, is a reimageable medium comprising: a substrate; and a photochromic material, wherein the medium is capable of exhibiting a color contrast and an absence of the color contrast, wherein the medium has a characteristic that when the medium exhibits the absence of the color contrast and is then exposed to an imaging light corresponding to a predetermined image to result in an exposed region and a non-exposed region, the color contrast is present between the exposed region and the non-exposed region to form a temporary image corresponding to the predetermined image that is visible for a visible time, wherein the medium has a characteristic that when the temporary image is exposed to an indoor ambient condition for an image erasing time, the color contrast changes to the absence of the color contrast to erase the temporary image in all of the following: (i) when the indoor ambient condition includes darkness at ambient temperature, (ii) when the indoor ambient condition includes indoor ambient light at ambient temperature, and (iii) when the indoor ambient condition includes both the darkness at ambient temperature and the indoor ambient light at ambient temperature, and wherein the medium is capable of undergoing multiple cycles of temporary image formation and temporary image erasure.

Disclosed in commonly assigned U.S. patent application Ser. No. 11/220,803, filed Sep. 8, 2005, is an image forming medium, comprising: a substrate; and an imaging layer comprising a photochromic material and a polymer binder coated on said substrate, wherein the photochromic material exhibits a reversible homogeneous-heterogeneous transition between a colorless state and a colored state in the polymer binder.

Disclosed in commonly assigned U.S. patent application Ser. No. 11/220,572, filed Sep. 8, 2005, is an image forming medium, comprising: a substrate; and a mixture comprising a photochromic material and a solvent wherein said mixture is coated on said substrate, wherein the photochromic material exhibits a reversible homogeneous-heterogeneous transition between a colorless state and a colored state in the solvent.

Disclosed in commonly assigned U.S. patent application Ser. No. 11/123,163, filed May 6, 2005, is an image forming medium, comprising a polymer; and a photochromic compound containing chelating groups embedded in the polymer; and a metal salt; wherein molecules of the photochromic compound are chelated by a metal ion from the metal salt.

Disclosed in commonly assigned U.S. patent application Ser. No. 11/093,993, filed Mar. 20, 2005, is a reimageable medium, comprising: a substrate having a first color; a photochromic layer adjacent to the substrate; a liquid crystal layer adjacent to the photochromic layer, wherein the liquid crystal layer includes a liquid crystal composition; and an electric field generating apparatus connected across the liquid crystal layer, wherein the electric field generating apparatus supplies a voltage across the liquid crystal layer.

Disclosed in commonly assigned U.S. patent application Ser. No. 10/834,529, filed Apr. 29, 2004, is a reimageable medium for receiving an imaging light having a predetermined wavelength scope, the medium comprising: a substrate; a photochromic material capable of reversibly converting among a number of different forms, wherein one form has an absorption spectrum that overlaps with the predetermined wavelength scope; and a light absorbing material exhibiting a light absorption band with an absorption peak, wherein the light absorption band overlaps with the absorption spectrum of the one form.

The entire disclosure of the above-mentioned applications are totally incorporated herein by reference.

BACKGROUND

Inkjet printing is a well-established market and process, where images are formed by ejecting droplets of ink in an image-wise manner onto a substrate. Inkjet printers are widely used in home and business environments, and particularly in home environments due to the low cost of the inkjet printers. The inkjet printers generally allow for producing high quality images, ranging from black-and-white text to photographic images, on a ride range of substrates such as standard office paper, transparencies, and photographic paper.

However, despite the low printer costs, the cost of replacement inkjet cartridges can be high, and sometimes higher than the cost of the printer itself. These cartridges must be replaced frequently, and thus replacement costs of the ink cartridges is a primary consumer complaint relating to inkjet printing.

Reducing ink cartridge replacement costs would thus be a significant enhancement to inkjet printing users.

In addition, many paper documents are promptly discarded after being read. Although paper is inexpensive, the quantity of discarded paper documents is enormous and the disposal of these discarded paper documents raises significant cost and environmental issues. Accordingly, there is a continuing desire for providing a new medium for containing the desired image, and methods for preparing and using such a medium. In aspects thereof it would be desirable to be reusable, to abate the cost and environmental issues, and desirably also is flexible and paper-like to provide a medium that is customarily acceptable to end-users and easy to use and store.

Although there are available technologies for transient image formation and storage, they generally provide less than desirable results for most applications as a paper substitute. For example, alternative technologies include liquid crystal displays, electrophoretics, and gyricon image media. However, these alternative technologies may not in a number of instances provide a document that has the appearance and feel of traditional paper, while providing the desired reimageability.

Imaging techniques employing photochromic materials, that is materials which undergo reversible or irreversible photoinduced color changes are known, for example, U.S. Pat. No. 3,961,948 discloses an imaging method based upon visible light induced changes in a photochromic imaging layer containing a dispersion of at least one photochromic material in an organic film forming binder.

These and other photochromic (or reimageable or electric) papers are desirable because they can provide imaging media that can be reused many times, to transiently store images and documents. For example, applications for photochromic based media include reimageable documents such as, for example, electronic paper documents. Reimageable documents allow information to be kept for as long as the user wants, then the information can be erased or the reimageable document can be re-imaged using an imaging system with different information.

Although the above-described approaches have provided reimageable transient documents, there is a desire for reimageable paper designs that provide longer image life-times, and more desirable paper-like appearance and feel. For example, while the known approaches for photochromic paper provide transient visible images, the visible images are very susceptible to UV, such as is present in both ambient interior light and more especially in sun light, as well as visible light. Due to the presence of this UV and visible light, the visible images are susceptible to degradation by the UV light, causing the unimaged areas to darken and thereby decrease the contrast between the desired image and the background or unimaged areas.

That is, a problem associated with transient documents is the sensitivity of the unimaged areas to ambient UV-VIS light (such as <420 nm) where the photochromic molecule absorbs. Unimaged areas become colored after a period of time, decreasing the visual quality of the document, because the contrast between white and colored state is reduced. One approach, described in the above-referenced U.S. patent application Ser. No. 10/834,529, is to stabilize the image against light of wavelength <420 nm by creating a band-pass window for the incident light capable of isomerising (i.e. inducing coloration) in the material, centered around 365 nm. However, the unimaged areas of the documents still are sensitive to UV-VIS light of wavelength centered around 365 nm.

Disclosed in U.S. Pat. No. 7,057,054 is a photochromic material having a ring opening quantum yield of $10^{-3}$ or lower which does not fade under ambient light. The material comprises a compound belonging to the diheteroarylethene class. The compound has alkoxy group and aryl group on the heteroaryl group.

SUMMARY

It is desirable for some uses that an image formed on a reimageable paper remains stable for extended time period, without the image or image contrast being degraded by exposure to ambient UV light. However, it is also desired that the image can be erased when desired, to permit reimaging of the paper. Electronic paper documents should maintain a written image for as long as the user needs to view it, without the image being degraded by ambient light. The image may then be erased or replaced with a different image by the user on command.

The present disclosure addresses these and other needs, in embodiments, by providing a reimageable paper utilizing a composition that is both imageable and eraseable by heat and light, and which comprises an alkoxy substituted diarylethene dispersed in a solvent or polymeric binder, where the composition exhibits a reversible transition between a colorless and a colored state. Imaging is conducted by applying UV light and optional heat to the imaging material to cause a color change, and erasing is conducted by applying visible light and optionally heat to the imaging material to reverse the color change. The present disclosure in other embodiments provides an inkless printing method using the reimageable inkless printing papers, and apparatus and systems for such printing.

The present disclosure thereby provides a printing media, method, and printer system for printing images without using ink or toner. The paper media has a special imageable composition and it is printed and can be erased with light and heat. The paper media thus allows image formation and erasure using a printer that does not require ink or toner replacement, and instead images the paper using a UV light source, such as a LED. The compositions and methods of the present disclosure also provide transient images that last for significantly longer periods of time, such as two days or more, before self-erase occurs. These advantages, and others, allow wider application of the reimageable transient documents.

In an embodiment, the present disclosure provides an image forming medium, comprising
  a paper substrate; and
    an imaging layer coated on or impregnated into said paper substrate, wherein the imaging layer comprises an imaging composition comprising an alkoxy substituted diarylethene dissolved or dispersed in a solvent or polymeric binder;
  wherein the imaging composition exhibits a reversible transition between a colorless and a colored state.

In another embodiment, the present disclosure provides a method of making an image forming medium, comprising applying an imaging layer composition to a paper substrate, wherein the imaging layer composition comprises an alkoxy substituted diarylethene dissolved or dispersed in said solvent or polymeric binder;
  wherein the imaging layer composition exhibits a reversible transition between a colorless and a colored state.

In another aspect, the present disclosure provides a method of forming an image, comprising:
  providing an image forming medium comprising:
    a paper substrate; and
    an imaging layer coated on or impregnated into said paper substrate, wherein the imaging layer comprises an imaging composition comprising an alkoxy substituted diarylethene dissolved or dispersed in a solvent or polymeric binder, wherein the imaging composition exhibits a reversible transition between a colorless and a colored state; and exposing the image forming medium to UV irradiation of a first wavelength in an imagewise manner to form a visible image.

The imaging method can be conducted, for example, using an imaging system, comprising:

the above image forming medium; and a printer comprising an irradiation source that sensitizes the photochromic material to convert the photochromic material from a colorless state to a colored state.

DETAILED DESCRIPTION OF EXEMPLARY EMBODIMENTS

Generally, in various exemplary embodiments, there is provided an inkless reimageable paper formed using a composition that is imageable and eraseable by heat and light, such as comprising a photochromic material that is an alkoxy substituted diarylethene dispersed in a solvent or polymeric binder, where the composition exhibits a reversible transition between a colorless and a colored state. Exposing the imaging layer to a first stimulus such as UV light irradiation causes the photochromic material to convert from the colorless state to a colored state. Likewise, exposing the imaging layer to a second stimulus such as visible light irradiation and optional heat causes the photochromic material to convert from the colored state to the colorless state. By a colored state, in embodiments, refers to for example, the presence of visible wavelengths; likewise, by a colorless state, in embodiments, refers to for example, the complete or substantial absence of visible wavelengths.

Photochromism and thermochromism are defined as the reversible photocoloration of a molecule from exposure to light (electromagnetic radiation) and heat (thermal radiation) based stimuli respectively. Typically photochromic molecules undergo structural and/or electronic rearrangements when irradiated with UV light that converts them to a more conjugated colored state. In the case of photochromic molecules, the colored state can typically be converted back to their original colorless state by irradiating them with visible light. In some cases thermal energy can also be used to decolorize a photochrome. If the interconversion is also capable thermally (by applying heat), as is the case in alkoxy substituted dithienylethenes, spiropyrans, azabenzenes, schiff bases and the like, the molecules are classified as both thermochromic and photochromic. Photochromic compounds are bi-stable in absence of light whereas photochromic-thermochromic hybrid compounds can also fade in the absence of light through a thermal process to the thermodynamically more stable colorless state. To create a stable reimageable document it is desired to stabilize the colored state, specifically to ambient conditions that the document will encounter in everyday life, such as broad band light and various heating/cooling conditions.

In embodiments, the image forming medium generally comprises an imaging layer coated on or impregnated in a suitable paper substrate material, or sandwiched or laminated between a first and a second substrate material (i.e., a paper substrate material and an overcoat layer). The imaging layer comprises an improved photochromic and thermochromic material that is an alkoxy substituted diarylethene dispersed in a solvent or polymeric binder and that provides increased thermal stability in the colored state. The improved photochromic material is dispersed in a solvent or a polymeric binder, and exhibits a reversible transition between a colorless state and a colored state in response to heat and light.

The imaging layer can include any suitable photochromic material and solvent or polymer binder. For example, the photochromic material and solvent or polymer binder are selected such that when the photochromic material is dissolved or dispersed in the solvent or polymer binder, the photochromic material is in its clear state. However, when the photochromic material is exposed to a first stimulus, such as ultraviolet light, the photochromic material isomerizes to a more polar colored form. This color change can be reversed, and thus the image "erased" and the photochromic paper returned to a blank state, by various means such as by applying a second stimulus such as visible light and/or heat that reverses the isomerization reaction. In the colored state, the image can remain visible for a period of two days or more, such as a week or more or a month or more, providing increased usefulness of the photochromic paper.

In embodiments, the photochromic material is an alkoxy substituted diarylethene dispersed in a solvent or polymeric binder, where the photochromic material exhibits a reversible transition between a colorless and a colored state. The photochromic material exhibits photochromism, which is a reversible transformation of a chemical species induced in one or both directions by absorption of an electromagnetic radiation between two forms having different absorption spectra. The first form is thermodynamically stable and may be induced by absorption of light such as ultraviolet light to convert to a second form. The reverse reaction from the second form to the first form may occur, for example, thermally, or by absorption of light such as visible light, or both. Various exemplary embodiments of the photochromic material may also encompass the reversible transformation of the chemical species among three or more forms in the event it is possible that reversible transformation occurs among more than two forms. The photochromic material of embodiments may be composed of one, two, three, four, or more different types of photochromic materials, each of which has reversibly interconvertible forms. As used herein, the term "photochromic material" refers to all molecules of a specific species of the photochromic material, regardless of their temporary isomeric forms. In various exemplary embodiments, for each type of photochromic material, one form may be colorless or weakly colored and the other form may be differently colored.

In embodiments, the reimageable paper also generally comprises a solvent or polymer binder mixture of a photochromic material dispersed or dissolved in a solvent or polymer binder, with the mixture coated on a suitable paper substrate material, or sandwiched between a first and a second substrate material, one of which materials is paper. If desired, the mixture can be further constrained on the substrate material, or between the first and second substrate materials, such as by microencapsulating the solvent mixture, or the like.

The overwhelming majority of dithienylethene photochromes that appear in the literature are substituted with alkyl groups (typically methyl) at the 2-thienyl position. These compounds can be rapidly colored with UV light and decolored with visible light and are thermally stable chromophores in both states. These compounds, represented by a 2-thienyl methyl dithienylethene, can be represented as:

See, for example, "Dithienylethenes for Memories and Switches", Chem. Rev., 100, 1685-1716. However 2-thienyl alkoxy substituted dithienylethenes, where the methyl group is replaced by and alkoxy group, have been found to increase the stability of the colored states to visible light for longer periods while at the same time lowering the barrier to thermal de-colorization. See, for example, "Dithienylethenes with a Novel Photochromic Performance", J. Org. Chem., 2002, 67, 4574-4578, and U.S. Pat. No. 7,057,054, the entire disclosures of which are incorporated herein by reference.

Accordingly, the substituted diarylethene suitable for use in embodiments are those that can be represented by the following general formulas:

[I]

In formula [I], X independently represents H; a halogen such as chlorine, fluorine, bromine, or the like; a straight or branched, substituted or unsubstituted, alkyl group of from 1 to about 20 or to about 40 carbon atoms, such as methyl, ethyl, propyl, butyl, or the like, where the substitutions can include halogen atoms, hetero atoms (such as oxygen groups, nitrogen groups, and the like), and the like.

[II]

In formula [II], X represents S or O.

[III]

[IV]

In formula [IV], X represents S, O or C=O, Y represents O, $CH_2$ or C=O.

[V]

In formula [V], Y represents $CH_2$ or C=O.

[VI]

In formula [VI], X represents CH or N.

[VII]

In formula [VII], Y represents $CH_2$ or C=O.

In the general formulas [I]-[VII], $R_4$, $R_5$ are each independently selected from an alkyl group, including substituted alkyl groups, unsubstituted alkyl groups, linear alkyl groups, and branched alkyl groups, and wherein hetero atoms such as oxygen, nitrogen, sulfur, silicon, phosphorus, boron, and the like either may or may not be present in the alkyl group, a halogen group, an alkoxy group, a cyano group, a nitro group, an amino group, an amide group, an aryl group, an alkylaryl group, including substituted alkylaryl groups, unsubstituted alkylaryl groups, and wherein hetero atoms either may or may not be present in the alkyl portion of the alkylaryl group or the aryl portion of the alkylaryl group, $R_6$ represents an alkyl group, including substituted alkyl groups, unsubstituted alkyl groups, linear alkyl groups, and branched alkyl groups, and wherein hetero atoms such as oxygen, nitrogen, sulfur, silicon, phosphorus, boron, and the like either may or may not be present in the alkyl group, A represents substituents [a] or [b] or [c], and B represents substituents [d] or [e] or [f] shown below, In substituents [a]-[c], $R_4$ represents an aryloxy group including phenyl, naphthyl and the like and substituted and unsubstituted heteroaromatic group, an alkoxy group or substituted alkoxy group where the alkyl portion of the alkoxy group represents a straight, branched or cyclic, substituted or unsubstituted, alkyl group of from 1 to about 20 or about 40 carbon atoms, such as methyl, ethyl, propyl, butyl, isopropyl, cyclohexyl, isoborneol or the like, where the substitutions can include halogen atoms, hetero atoms (such as oxygen groups, nitrogen groups, and the like), and the like, $R_5$ represents an aryl group, or an alkylaryl group including substituted alkylaryl groups, unsubstituted alkylaryl groups, and wherein hetero atoms either may or may not be present in the alkyl portion of the alkylaryl group or the aryl portion of the alkylaryl, a cyano group, a carboxylic acid group or an unsaturated alkene group, $R_6$ represents a hydrogen atom, an alkyl group, a halogen atom, and alkoxy group, a fluoroalkyl group, a cyano group, an aryl group, or a substituted alkylaryl group, $R_7$ represents an alkyl group and aryl group, or an alkylaryl group including substituted alkylaryl groups, unsubstituted alkylaryl groups, and wherein hetero atoms either may or may not be present in the alkyl portion of the alkylaryl group or the aryl portion of the alkylaryl and U represents O or S.

In substituents [d]-[f], $R_8$ represents an aryloxy group including phenyl, napthyl and the like, and substituted and unsubstituted heteroaromatic group, or an alkoxy group or substituted alkoxy group where the alkyl portion of the alkoxy group represents a straight, branched or cyclic, substituted or unsubstituted, alkyl group of from 1 to about 20 or about 40 carbon atoms, such as methyl, ethyl, propyl, butyl, isopropyl, cyclohexyl, isoborneol or the like, where the substitutions can include halogen atoms, hetero atoms (such as oxygen groups, nitrogen groups, and the like), and the like, $R_9$ represents an aryl group, or an alkylaryl group including substituted alkylaryl groups, unsubstituted alkylaryl groups, and wherein hetero atoms either may or may not be present in the alkyl portion of the alkylaryl group or the aryl portion of the alkylaryl, a cyano group, a carboxylic acid group or an unsaturated alkene group, $R_{10}$ represents a hydrogen atom, an alkyl group, a halogen atom, and alkoxy group, a fluoroalkyl group, a cyano group, an aryl group, or a substituted alkylaryl group, R represents an alkyl group and aryl group, or an alkylaryl group including substituted alkylaryl groups, unsubstituted alkylaryl groups, and wherein hetero atoms either may or may not be present in the alkyl portion of the alkylaryl group or the aryl portion of the alkylaryl and Z represents O or S.

In certain embodiments, the substituted diarylethenes of formulas [I]-[VII] are those compounds where $R_4$ and $R_8$ are the same alkoxy containing substituents. In this case it is necessary for the alkyl or substituted alkyl groups to contain 4 or more carbon atoms. This is a requirement for adequate thermal-based cycloreversion reaction times for the present applications. In other embodiments, however, the alkoxy substituents of $R_4$ and $R_8$ can be different alkoxy substituents. In this case as well, it is preferred that either at least one or both of the alkoxy groups contain 4 or more carbon atoms.

2-Thienyl alkoxy containing diarylethenes are more stable in their colored states than other substituted diarylethenes, such as alkyl substituted diarylethenes, to visible light for longer periods of time. At the same time, the alkoxy substitution lowers the barrier to thermal de-colorization, or the reverse isomerization from the colored state back to the colorless state. These are important attributes for reusable paper document media, and have been found to be very specific to the alkoxy containing dithienylethene class of photochromes. For example, for some users, particularly those concerned with security of the information left unattended, self-erasing of a reimageable document in about a day is beneficial. However, for other users, self-erasing is a disadvantage because the users do not have control over the erasing time/rate. These latter users would prefer an "erase-on-demand" type of reusable document, where the document displays the printed image for as long as needed (for example, for several days to several weeks or more), then when the user decides, the information is erased during the re-printing process with new information on the same sheet of paper.

A particular advantage of alkoxy modified diarylethenes is that suitable selection of the alkoxy substituent can allow for specific tuning of the barrier to thermal erase. For example, the barrier to thermal erasing can be tuned to be rapid and complete at elevated temperatures (such as about 80 to about 160° C.) while maintaining long-term thermal-based color stability at ambient temperatures (such as about 25 to about 70° C.) based on the structure of the alkoxy R-group substituent. Based on thermal and spectroscopic analysis, the half-life thermal stability of specific compounds can be predicted to range from approximately 2.2 hours at 30° C. for the least thermally stable tert-butyl compound (See: Chem. Lett, 2002, 572.) to 420 years at 30° C. for the methoxy compound.

Accordingly, in some embodiments, the alkoxy modified dithienylethene photochromic material can be readily converted from its colored state to its colorless state by exposure to suitable irradiation, such as visible light, alone. However, in other embodiments, the alkoxy modified dithienylethene photochromic material can be readily converted from its colored state to its colorless state by exposure to suitable irradiation, such as visible light, in combination with heat, or by exposure to heat alone. By "readily converted" herein is meant that the photochromic material as prepared can be converted from its colored state to its colorless state in a period of less than about 30 minutes, less than about 10 minutes, less than about 1 minute, or less than about 30 seconds of exposure time to the suitable conversion means of heat and/or light. In contrast, by "not readily converted" herein is meant that the photochromic material as prepared is not converted from its colored state to its colorless state in a period of less than about 1 hour, such as less than about 1 week, less than about 1 year, or less than about 5 years, of exposure time to the suitable conversion means of heat and/or light. For example, in some embodiments where heat is used as the activator for the conversion, heating of the photochromic material at temperatures of from about 80 to about 250° C., such as from about 100 to about 200° C. or about 100 to about 160° C., can readily convert the photochromic material from the colored state back to the colorless state in the above time periods, while heating of the photochromic material at temperatures of from about 25 to about 70° C. does not readily convert the photochromic material from the colored state back to the colorless state.

These photochromic materials are thus different from other photochromic materials, including other differently substituted or unsubstituted dithienylethenes, in that the materials are generally not readily convertible back from the colored state to the colorless state by exposure to visible light alone, but require exposure to appropriate heating, with or without visible light in order to convert back from the colored state to the colorless state. This allows for a desirable product because the colored state can be frozen until sufficient heat beyond that of ambient heat induces enough molecular and lattice mobility to allow the structural reorganization to occur. In addition, in embodiments, the photochromic material requires only application of heat, and not light stimulus, to cause the photochromic material to switch between the colored and colorless states.

The image forming material (photochromic material) is dissolved or dispersed in any suitable carrier, such as a solvent, a polymer binder, or the like. Suitable solvents include, for example, straight chain aliphatic hydrocarbons, branched chain aliphatic hydrocarbons, and the like, such as where the straight or branched chain aliphatic hydrocarbons have from about 1 to about 30 carbon atoms. For example, a non-polar liquid of the ISOPAR™ series (manufactured by the Exxon Corporation) may be used as the solvent. These hydrocarbon liquids are considered narrow portions of isoparaffinic hydrocarbon fractions. For example, the boiling range of ISOPAR G™ is from about 157° C. to about 176° C.; ISOPAR H™ is from about 176° C. to about 191° C.; ISOPAR K™ is from about 177° C. to about 197° C.; ISOPAR L™ is from about 188° C. to about 206° C.; ISOPAR M™ is from about 207° C. to about 254° C.; and ISOPAR V™ is from about 254.4° C. to about 329.4° C. Other suitable solvent materials include, for example, the NORPAR™ series of liquids, which are compositions of n-paraffins available from Exxon Corporation, the SOLTROL™ series of liquids available from the Phillips Petroleum Company, and the SHELLSOL™ series of liquids available from the Shell Oil Company. Mixtures of one or more solvents, i.e., a solvent system, can also be used, if desired. In addition, more polar solvents can also be used. Examples of more polar solvents that may be used include halogenated and nonhalogenated solvents, such as tetrahydrofuran, trichloro- and tetrachloroethane, dichloromethane, chloroform, monochlorobenzene, toluene, xylenes, acetone, methanol, ethanol, xylenes, benzene, ethyl acetate, dimethylformamide, cyclohexanone, N-methyl acetamide and the like. The solvent may be composed of one, two, three or more different solvents. When two or more different solvents are present, each solvent may be present in an equal or unequal amount by weight ranging for example from about 5% to 90%, particularly from about 30% to about 50%, based on the weight of all solvents.

Both compositions dispersable in either organic polymers or waterborne polymers can be used, depending on the used components. For example, for waterborne compositions, polyvinylalcohol is a suitable application solvent, and polymethylmethacrylate is suitable for organic soluble compositions.

Suitable examples of polymer binders include, but are not limited to, polyalkylacrylates like polymethyl methacrylate (PMMA), polycarbonates, polyethylenes, oxidized polyethylene, polypropylene, polyisobutylene, polystyrenes, poly (styrene)-co-(ethylene), polysulfones, polyethersulfones, polyarylsulfones, polyarylethers, polyolefins, polyacrylates, polyvinyl derivatives, cellulose derivatives, polyurethanes, polyamides, polyimides, polyesters, silicone resins, epoxy resins, polyvinyl alcohol, polyacrylic acid, and the like. Copolymer materials such as polystyrene-acrylonitrile, polyethylene-acrylate, vinylidenechloride-vinylchloride, vinylacetate-vinylidene chloride, styrene-alkyd resins are also examples of suitable binder materials. The copolymers may be block, random, or alternating copolymers. In some embodiments, polymethyl methacrylate or a polystyrene is the polymer binder, in terms of their cost and wide availability. The polymer binder, when used, has the role to provide a coating or film forming composition.

Phase change materials can also be used as the polymer binder. Phase change materials are known in the art, and include for example crystalline polyethylenes such as Polywax® 2000, Polywax® 1000, Polywax® 500, and the like from Baker Petrolite, Inc.; oxidized wax such as X-2073 and Mekon wax, from Baker-Hughes Inc.; crystalline polyethylene copolymers such as ethylene/vinyl acetate copolymers, ethylene/vinyl alcohol copolymers, ethylene/acrylic acid copolymers, ethylene/methacrylic acid copolymers, ethylene/carbon monoxide copolymers, polyethylene-b-polyalkylene glycol wherein the alkylene portion can be ethylene, propylene, butylenes, pentylene or the like, and including the polyethylene-b-(polyethylene glycol)s and the like; crystalline polyamides; polyester amides; polyvinyl butyral; polyacrylonitrile; polyvinyl chloride; polyvinyl alcohol hydrolyzed; polyacetal; crystalline poly(ethylene glycol); poly(ethylene oxide); poly(ethylene therephthalate); poly(ethylene succinate); crystalline cellulose polymers; fatty alcohols; ethoxylated fatty alcohols; and the like, and mixtures thereof.

In general, most any organic polymer can be used. However, in embodiments, because heat is used to erase the visible image, the polymer can be selected such that it has thermal properties that can withstand the elevated temperatures that may be used for erasing formed images based on the specific alkoxy substituted diarylethene photochrome that is chosen.

In embodiments, the imaging composition can be applied in one form, and dried to another form for use. Thus, for example, the imaging composition comprising photochromic material and solvent or polymer binder may be dissolved or dispersed in a solvent for application to or impregnation into a paper substrate, with the solvent being subsequently evaporated to form a dry layer.

In general, the imaging composition can include the carrier and imaging material in any suitable amounts, such as from about 5 to about 99.5 percent by weight carrier, such as from about 30 to about 70 percent by weight carrier, and from about 0.05 to about 50 percent by weight photochromic material, such as from about 0.1 to about 5 percent photochromic material by weight.

For applying the imaging layer to the image forming medium paper substrate, the image forming layer composition can be applied in any suitable manner. For example, the image forming layer composition can be mixed and applied with any suitable solvent or polymer binder, and subsequently hardened or dried to form a desired layer. Further, the image forming layer composition can be applied either as a separate distinct layer to the supporting paper substrate, or it can be applied so as to impregnate into the supporting paper substrate.

The image forming medium may comprise a supporting paper substrate, coated or impregnated on at least one side with the imaging layer. As desired, the substrate can be coated or impregnated on either only one side, or on both sides, with the imaging layer. When the imaging layer is coated or impregnated on both sides, or when higher visibility of the image is desired, an opaque layer may be included between the supporting substrate and the imaging layer(s) or on the opposite side of the supporting paper substrate from the coated imaging layer. Thus, for example, if a one-sided image forming paper medium is desired, the image forming medium may include a supporting paper substrate, coated or impregnated on one side with the imaging layer and coated on the other side with an opaque layer such as, for example, a white layer. Also, the image forming medium may include a supporting paper substrate, coated or impregnated on one side with the imaging layer and with an opaque layer between the substrate and the imaging layer. If a two-sided image forming medium is desired, then the image forming medium may include a supporting paper substrate, coated or impregnated on both sides with the imaging layer, and with at least one opaque layer interposed between the two coated imaging layers. Of course, an opaque supporting paper substrate, such as conventional paper, may be used in place of a separate supporting substrate and opaque layer, if desired.

Any suitable supporting paper substrate may be used. The paper may be, for example, plain paper such as XEROX® 4024 paper, ruled notebook paper, bond paper, silica coated papers such as Sharp Company silica coated paper, Jujo paper, and the like. The substrate may be a single layer or multi-layer where each layer is the same or different material. In embodiments, the substrate has a thickness ranging for example from about 0.3 mm to about 5 mm, although smaller or greater thicknesses can be used, if desired.

When an opaque layer is used in the image forming medium, any suitable material may be used. For example, where a white paper-like appearance is desired, the opaque layer may be formed from a thin coating of titanium dioxide, or other suitable material like zinc oxide, inorganic carbonates, and the like. The opaque layer can have a thickness of, for example, from about 0.01 mm to about 10 mm, such as about 0.1 mm to about 5 mm, although other thicknesses can be used.

If desired, a further overcoating layer may also be applied over the applied imaging layer. The further overcoating layer may, for example, be applied to further adhere the underlying layer in place over the substrate, to provide wear resistance, to improve appearance and feel, and the like. The overcoating layer can be the same as or different from the substrate material, although in embodiments at least one of the overcoating layer and substrate paper layer is clear and transparent to permit visualization of the formed image. The overcoating layer can have a thickness of, for example, from about 0.01 mm to about 10 mm, such as about 0.1 mm to about 5 mm, although other thicknesses can be used. For example, if desired or necessary, the coated substrate can be laminated between supporting sheets such as plastic sheets.

In embodiments where the imaging material is coated on or impregnated into the paper substrate, the coating can be conducted by any suitable method available in the art, and the coating method is not particularly limited. For example, the imaging material can be coated on or impregnated into the paper substrate by dip coating the paper substrate into a solution of the imaging material composition followed by any necessary drying, or the paper substrate can be coated with the imaging composition to form a layer thereof. Similarly, the protective coating can be applied by similar methods.

Where the photochromic material is mixed with a solvent applied on the paper substrate, and where the solvent system is retained in the final product, additional processing may be required. As a result, where the photochromic material is simply coated on the paper substrate, a cover material is generally applied over the solvent system to constrain the solvent system in place on the substrate. Thus, for example, the cover material can be a solid layer, such as any of the suitable materials disclosed above for the substrate layer. In an alternative embodiment, a polymer material or film may be applied over the photochromic material, where the polymer film penetrates the photochromic material at discrete points to in essence form pockets or cells of photochromic material that are bounded on the bottom by the substrate and on the sides and top by the polymeric material. The height of the cells can be, for example, from about 1 micron to about 1000 microns, although not limited thereto. The cells can be any shape, for example square, rectangle, circle, polygon, or the like. In these embodiments, the cover material is advantageously transparent and colorless, to provide the full color contrast effect provided by the photochromic material.

In another embodiment, the solvent system with the photochromic material can be encapsulated or microencapsulated, and the resultant capsules or microcapsules deposited or coated on the paper substrate as described above. Any suitable encapsulation technique can be used, such as simple and complex coacervation, interfacial polymerization, in situ polymerization, phase separation processes. For example, a suitable method if described for ink materials in U.S. Pat. No. 6,067,185, the entire disclosure of which is incorporated herein by reference and can be readily adapted to the present disclosure. Useful exemplary materials for simple coacervation include gelatin, polyvinyl alcohol, polyvinyl acetate and cellulose derivatives. Exemplary materials for complex coacervation include gelatin, acacia, acrageenan, carboxymethylecellulose, agar, alginate, casein, albumin, methyl vinyl ether-co-maleic anhydride. Exemplary useful materials for interfacial polymerization include diacyl chlorides such as sebacoyl, adipoyl, and di or poly-amines or alcohols and isocyanates. Exemplary useful materials for in situ polymerization include for example polyhydroxyamides, with aldehydes, melamine or urea and formaldehyde; water-soluble oligomers of the condensate of melamine or urea and formaldehyde, and vinyl monomers such as for example styrene, methyl methacrylate and acrylonitrile. Exemplary useful materials for phase separation processes include polystyrene, polymethylmethacrylate, polyethylmethacrylate, ethyl cellulose, polyvinyl pyridine and polyacrylonitrile. In these embodiments, the encapsulating material is also transparent and colorless, to provide the full color contrast effect provided by the photochromic material.

Where the photochromic material is encapsulated, the resultant capsules can have any desired average particle size. For example, suitable results can be obtained with capsules having an average size of from about 2 to about 1000 microns, such as from about 10 to about 600 or to about 800 microns, or from about 20 to about 100 microns, where the average size refers to the average diameter of the microcapsules and can be readily measured by any suitable device such as an optical microscope. For example, in embodiments, the capsules are large enough to hold a suitable amount of photochromic material to provide a visible effect when in the colored form, but are not so large as to prevent desired image resolution.

In its method aspects, the present disclosure involves providing an image forming medium comprised of a paper substrate and an imaging layer comprising an alkoxy substituted dithienylethene dispersed in a solvent or polymeric binder, where the composition exhibits a reversible transition between a colorless and a colored state. To provide separate writing and erasing processes, imaging is conducted by applying a first stimulus, such as UV light irradiation, to the imaging material to cause a color change, and erasing is conducted by applying a second, different stimulus, such as UV or visible light irradiation, and optionally heat, to the imaging material to reverse the color change. In other embodiments, the erasing is conducted by applying both visible light and heat, or by applying heat alone. Thus, for example, the imaging layer as a whole could be sensitive at a first (such as UV) wavelength that causes the photochromic material to convert from a clear to a colored state, while the imaging layer as a whole could be sensitive at a second, different (such as visible) wavelength and/or to heat that causes the photochromic material to convert from the colored back to the clear state.

In embodiments, heating can be applied to the imaging layer before or at the same time as the light irradiation, for either the writing and/or erasing processes. However, in embodiments, heating is not required for the writing process, as such stimuli as UV light irradiation are sufficient to cause the color change from colorless to colored, while heating may be desired or required for the erasing process to assist in increasing material mobility for speeding the color change from colored to colorless. When used, the heat raises the temperature of the imaging composition, particularly the photochromic material, to raise the mobility of the imaging composition and thus allow easier and faster conversion from one color state to the other. The heating can be applied before or during the irradiation, or by itself, as long as the heating causes the imaging composition to be raised to the desired temperature during the irradiation or erasing process. Any suitable heating temperature can be used, and will depend upon, for example, the specific imaging composition used. For example, where the photochromic material is dispersed in a polymer or a phase change composition, the heating can be conducted to raise the polymer to at or near its glass transition temperature or melting point, such as within about 5° C., within about 10° C., or within about 20° C. of the glass transition temperature or melting point, although it is desired in certain embodiments that the temperature not exceed the melting point of the polymer binder so as to avoid undesired movement or flow of the polymer on the substrate.

The different stimuli, such as different light irradiation wavelengths, can be suitably selected to provide distinct writing and erasing operations. For example, in one embodiment, the photochromic material is selected to be sensitive to UV light to cause isomerization from the clear state to the colored state, but to be sensitive to visible light to cause isomerization from the colored state to the clear state. In other embodiments, the writing and erasing wavelengths are separated by at least about 10 nm, such as at least about 20 nm, at least about 30 nm, at least about 40 nm, at least about 50 nm, or at least about 100 nm. Thus, for example, if the writing wavelength is at a wavelength of about 360 nm, then the erasing wavelength is desirably a wavelength of greater than about 400 nm, such as greater than about 500 nm. Of course, the relative separation of sensitization wavelengths can be dependent upon, for example, the relatively narrow wavelengths of the exposing apparatus.

In a writing process, the image forming medium is exposed to an imaging light having an appropriate activating wavelength, such as a UV light source such as a light emitting diode (LED), in an imagewise fashion. The imaging light supplies sufficient energy to the photochromic material to cause the photochromic material to convert, such as isomerize, from a clear state to a colored state to produce a colored image at the imaging location, and for the photochromic material to isomerize to stable isomer forms to lock in the image. The amount of energy irradiated on a particular location of the image forming medium can affect the intensity or shade of color generated at that location. Thus, for example, a weaker intensity image can be formed by delivering a lesser amount of energy at the location and thus generating a lesser amount of colored photochromic unit, while a stronger intensity image can be formed by delivering a greater amount of energy to the location and thus generating a greater amount of colored photochromic unit. When suitable photochromic material, solvent or polymer binder, and irradiation conditions are selected, the variation in the amount of energy irradiated at a particular location of the image forming medium can thus allow for formation of grayscale images, while selection of other suitable photochromic materials can allow for formation of full color images.

Once an image is formed by the writing process, the formation of stable isomer forms of the photochromic material within the imaging materials locks in the image. That is, the isomer forms of the new photochromic materials are more stable to ambient heat and light, and thus exhibit greater long-term stability. The image is thereby "frozen" or locked in, and cannot be readily erased in the absence of a specific second stimuli. In embodiments, the image is locked in, and cannot be readily erased by ambient heat or light, and requires elevated temperature and or a light stimulus in order to revert back to the colorless state. The imaging substrate thus provides a reimageable substrate that exhibits a long-lived image lifetime, but which can be erased as desired and reused for additional imaging cycles.

In an erasing process, the writing process is essentially repeated, except that a different stimuli, such as a different wavelength irradiation light, such as visible light, is used, and/or when the photochromic material is optionally heated such as to a temperature at or near a glass transition, melting, or boiling point temperature of the carrier material. For example, the heating can be conducted at a temperature of from about 80 to about 250° C., such as from about 100 to about 200° C. or about 100 to about 160° C. The erasing process causes the isomerizations to reverse and the photochromic unit to convert, such as isomerize, from a colored state to a clear state to erase the previously formed image at the imaging location. The erasing procedure can be on an image-wise fashion or on the entire imaging layer as a whole, as desired. The heating step is optional, in that certain compositions can be provided that are erased upon only exposure to the selected stimulus such as light wavelength, while other compositions can be provided that can be erased only under a heating condition, optionally upon exposure to the selected stimulus such as light wavelength.

The separate imaging lights used to form the transient image may have any suitable predetermined wavelength scope such as, for example, a single wavelength or a band of wavelengths. In various exemplary embodiments, the imaging light is an ultraviolet (UV) light having a single wavelength or a narrow band of wavelengths. For example, the UV light can be selected from the UV light wavelength range of about 200 nm to about 475 nm, such as a single wavelength at about 365 nm or a wavelength band of from about 360 nm to about 370 nm. For forming the image, the image forming medium may be exposed to the respective imaging light for a time period ranging from about 10 milliseconds to about 5 minutes, particularly from about 30 milliseconds to about 1 minute. The imaging light may have an intensity ranging from about 0.1 mW/cm$^2$ to about 100 mW/cm$^2$, particularly from about 0.5 mW/cm$^2$ to about 10 mW/cm$^2$.

The erasing light is strong visible light of a wavelength which overlaps with the absorption spectrum of the colored state isomer in the visible region. For example the erasing useful light may have a wavelength ranging from about 400 nm to about 800 nm or more preferably form about 500 nm to about 800 nm. The usable Visible light of the erasing may be obtained form a Xenon light source with a bulb having a power from 5 W to about 1000 W or more preferably from about 20 W to about 200 W, which is placed in the proximity of the areas of the document which is to be erased. Another suitable erasing light source is an LED having a wavelength in the visible region of the light spectrum, as defined above. The erasing light may be having a single wavelength or a narrow band of wavelengths.

In various exemplary embodiments, imaging light corresponding to the predetermined image may be generated for example by a computer or a Light Emitting Diode (LED) array screen and the image is formed on the image forming medium by placing the medium on or in proximity to the LED screen for the desired period of time. In other exemplary embodiments, a UV Raster Output Scanner (ROS) may be used to generate the UV light in an image-wise pattern. This embodiment is particularly applicable, for example, to a printer device that can be driven by a computer to generate printed images in an otherwise conventional fashion. That is, the printer can generally correspond to a conventional inkjet printer, except that the inkjet printhead that ejects drops of ink in the imagewise fashion can be replaced by a suitable UV light printhead that exposes the image forming medium in an imagewise fashion. In this embodiment, the replacement of ink cartridges is rendered obsolete, as writing is conducted using a UV light source. The printer can also include a heating device, which can be used to apply heat to the imaging material to erase any existing images. Other suitable imaging techniques that can be used include, but are not limited to, irradiating a UV light onto the image forming medium through a mask, irradiating a pinpoint UV light source onto the image forming medium in an imagewise manner such as by use of a light pen, and the like.

For erasing an image in order to reuse the imaging substrate, in various exemplary embodiments, the substrate can be exposed to a suitable imaging light, to cause the image to be erased. Such erasure can be conducted in any suitable manner, such as by exposing the entire substrate to the erasing light at once, exposing the entire substrate to the erasing light in a successive manner such as by scanning the substrate, or the like. In other embodiments, erasing can be conducted at particular points on the substrate, such as by using a light pen, or the like.

According to various exemplary implementations, the color contrast that renders the image visible to an observer may be a contrast between, for example two, three or more different colors. The term "color" may encompass a number of aspects such as hue, lightness and saturation, where one color may be different from another color if the two colors differ in at least one aspect. For example, two colors having the same hue and saturation but are different in lightness would be considered different colors. Any suitable colors such as, for example, red, white, black, gray, yellow, cyan, magenta, blue, and purple, can be used to produce a color contrast as long as the image is visible to the naked eye of a user. However, in terms of desired maximum color contrast, a desirable color contrast is a dark gray or black image on a light or white background, such as a gray, dark gray, or black image on a white background, or a gray, dark gray, or black image on a light gray background.

In various exemplary embodiments, the color contrast may change such as, for example, diminish during the visible time, but the phrase "color contrast" may encompass any degree of color contrast sufficient to render an image discernable to a user regardless of whether the color contrast changes or is constant during the visible time.

An example is set forth herein below and is illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Example 1

A photochromic material of general formula [I] (3,3'-(perfluorocyclopent-1-ene-1,2-diyl)bis(2-methoxy-5-phenylthiophene)) where substituents [a] and [d] are the same and the alkoxy substituents of $R_4$ and $R_8$ contain fewer then 3 carbon atoms, was synthesized according to the procedure described in "Dithienylethenes with a Novel Photochromic Performance", J. Org. Chem., 2002, 67, 4574-4578.

Photochromic paper media was prepared as follows. A solution was made by dissolving 200 mg of the photochromic material in 10 ml of a solution of polymethylmethacrylate (PMMA-polymeric binder) dissolved in toluene (PMMA/Toluene=15 g/120 ml). The solution is then coated onto Xerox 4024 paper by doctor blade procedure. The coated paper was allowed to dry, to provide a reimageable paper media, ready for printing. Several sheets of paper were coated in this way.

One sheet of the coated paper was printed by illumination through a mask containing a text to be displayed, by exposure to UV light (4 mW/cm$^2$; 365 nm for 30 s). A blue printed image was produced. The image was of a blue intense color over a clear (slightly bluish) background. The contrast between printed areas and the background was very good. This paper was kept under ambient room light conditions for 4 weeks and there was no detectable fading of the colored imaged area. For comparison, a similar transient document prepared using a spiropyran as the photochromic material faded in about 16 hours under the same conditions. The image produced from the 3,3'-(perfluorocyclopent-1-ene-1,2-diyl) bis(2-methoxy-5-phenylthiophene) photochromic paper could be erased by heating the paper in an oven at 160 deg/C. for 50 min.

Example 2

A photochromic material (3,3'-perfluorocyclopent-1-ene-1,2-diyl)bis(2-(cyclohexyloxy)-5-phenylthiophene) where substituents [a] and [d] are the same and have greater than 3 carbon atoms on the alkoxy substituents of $R_4$ and $R_8$, was synthesized as described below. Attachment of 3-bromo-2-(cyclohexyloxy)-5-phenylthiophene to octaflurocyclopentene was preformed according to the procedure described in "Dithienylethenes with a Novel Photochromic Performance", J. Org. Chem., 2002, 67, 4574-4578.

Cyclohexyl 4-oxo-4-phenylbutanoate: In a 2 L 3-neck round-bottomed flask at ambient temperature was added 4-oxo-4-phenylbutanoic acid (41 g, 230 mmol) in dichloromethane (1.5 L) to give a colorless hazy solution. DCC (47.5 g, 230 mmol) was added, then cyclohexanol (23.05 g, 230 mmol) was added. The mixture was stirred at RT for 3 h and then DMAP was added (2.81 g, 23 mmol). The reaction was stirred at ambient temperature for 24 h and the solvent was concentrated to ~400 ml by distillation and the solution was then filtered to remove the white solid. The solution was subsequently concentrated and the residue purified by column chromatography (SiO$_2$) in CH$_2$Cl$_2$/Hexane 1:3 to give a colorless liquid (56 g) which was cyclohexyl 4-oxo-4-phenylbutanoate (88% yield).

2-(cyclohexyloxy)-5-phenylthiophene: In a 500 mL round-bottomed flask under argon was added cyclohexyl 4-oxo-4-phenylbutanoate (2 g, 7.68 mmol) and Lawesson reagent (3.73 g, 9.22 mmol) in anhydrous toluene (125 mL) to give a white suspension. The mixture was heated to reflux whereby the lawesson's reagent dissolved. The mixture was refluxed for ~24 h at which point the mixture was cooled and filtered. The filtrate was concentrated and placed on a short column of SiO$_2$ and flashed with CH$_2$Cl$_2$:Hex 1:3 yielding a white solid (1.4 g) which was 2-(cyclohexyloxy)-5-phenylthiophene (70%)

3-bromo-2-(cyclohexyloxy)-5-phenylthiophene: In a 250 mL round-bottomed flask cooled to 0° C. was added 2-(cyclohexyloxy)-5-phenylthiophene (1.071 g, 4.15 mmol). The mixture was stirred and NBS (N-Bromosuccinimide) (0.738 g, 4.15 mmol) in CH$_2$Cl$_2$ (75 mL) to give a colorless solution. The mixture was stirred at 0° C. for 1 h. The mixture was allowed to warm to ambient temperature. After 1 h at ambient temperature the mixture was concentrated and flashed through a plug of Silica (1:3, CH$_2$Cl$_2$:Hexane) yielding a white solid (1.25 g) which was 3-bromo-2-(cyclohexyloxy)-5-phenylthiophene (95%).

3,3'-perfluorocyclopent-1-ene-1,2-diyl)bis(2-(cyclohexyloxy)-5-phenylthiophene: In a 100 mL flame dried round-bottomed flask under argon at ambient temperature was added 3-bromo-2-(cyclohexyloxy)-5-phenylthiophene (0.905 g, 2.68 mmol) in anhydrous THF (60 ml) to give a light purple solution. The solution was cooled to −70° C. and n-Butyllithium 2.5M hexanes (1.073 ml, 2.68 mmol) was added dropwise over 2 min. The mixture turned light yellow and was stirred for 2 h at −70° C. Perfluorocyclopent-1-ene (0.176 ml, 1.315 mmol) was then added. The mixture was stirred for 30 min at −70° C. and then allowed to warm to ambient temperature and stirred for 1 h. Water and ether was added and the layers were separated. The ether layer was washed with saturated bicarbonate and then brine and dried with sodium sulfate. The ether was removed and the brown residue was purified by column chromatography (SiO$_2$) hexanes yielding a slightly green solid (0.35 g) which was 3,3'-perfluorocyclopent-1-ene-1,2-diyl)bis(2-(cyclohexyloxy)-5-phenylthiophene (20%).

Example 3

A photochromic material (2-tert-butoxy-3-(3,3,4,4,5,5-hexafluoro-2-(2-methoxy-5-phenylthiophen-3-yl)cyclopent-1-enyl)-5-phenylthiophene) where substituents [a] and [d] are different and where [a] has fewer than 3 carbon atoms on the alkoxy group R$_4$ and [d] has greater than 3 carbon atoms on the alkoxy substituent R$_8$ was synthesized as described below.

2-tert-butoxy-3-(3,3,4,4,5,5-hexafluoro-2-(2-methoxy-5-phenylthiophen-3-yl)cyclopent-1-enyl)-5-phenylthiophene: To a 250 mL flame dried round-bottomed flask under argon was added 3-bromo-2-methoxy-5-phenylthiophene (2.518 g, 9.36 mmol) in anhydrous THF (100 ml) to give a colorless solution. The mixture was cooled to −70 deg/C. and n-Butyllithium 2.5M hexanes (3.93 ml, 9.82 mmol) was added dropwise. The solution was stirred at −70 deg/C. for 45 min. In a separate flame dried 3 neck 500 mL round-bottomed flask under argon was added perfluorocyclopent-1-ene (4.02 ml, 29.9 mmol) in anhydrous THF (250 ml) to give a colorless solution. This mixture was also cooled to −70 deg/C. After 45 min the yellow 3-bromo-2-methoxy-5-phenylthiophene solution was cannulated into the perflurocyclopent-1-ene with under reduced pressure. The mixture was stirred at −70 deg/C. for 1 h. The mixture was concentrated to half volume and ether was added and the mixture washed with water and then brine. The residue was purified by column chromatography (SiO$_2$) with hexanes (54%).

2-tert-butoxy-3-(3,3,4,4,5,5-hexafluoro-2-(2-methoxy-5-phenylthiophen-3-yl)cyclopent-1-enyl)-5-phenylthiophene: To a flame dried 100 mL round-bottomed flask under argon was added 3-bromo-2-tert-butoxy-5-phenylthiophene (0.66 g, 2.121 mmol) (Chem. Lett. 2002, 572) in 50 ml of anhydrous THF to give a colorless solution. The mixture was then cooled to −70 deg/C. n-Butyllithium 2.5M hexanes (0.848 ml, 2.121 mmol) was added and the solution turned pale yellow. The mixture was stirred at −70 for 45 min and 2-methoxy-3-(perfluorocyclopent-1-enyl)-5-phenylthiophene (0.811 g, 2.121 mmol) dissolved in 2-3 ml of anhydrous THF was added dropwise. The mixture was allowed to stir for 1 h at −70 and then allowed to warm to ambient. The mixture was diluted with ether and washed with a saturated bicarbonate solution. The organic layer was then concentrated and the resulting residue was purified through SiO$_2$ (1:3 DCM:Hex) yielding a white solid which was 2-tert-butoxy-3-(3,3,4,4,5,5-hexafluoro-2-(2-methoxy-5-phenylthiophen-3-yl)cyclopent-1-enyl)-5-phenylthiophene (50%).

Example 4

A photochromic material (2-tert-butoxy-3-(2-(2-(cyclohexyloxy)-5-phenylthiophen-3-yl)-3,3,4,4,5,5-hexafluorocyclopent-1-enyl)-5-phenylthiophene) where substituents [a] and [d] are different and where [a] and [d] have greater than 3 carbon atoms on the alkoxy substituent R$_4$ and R$_8$ was synthesized similar to example 3.

Figure 1:
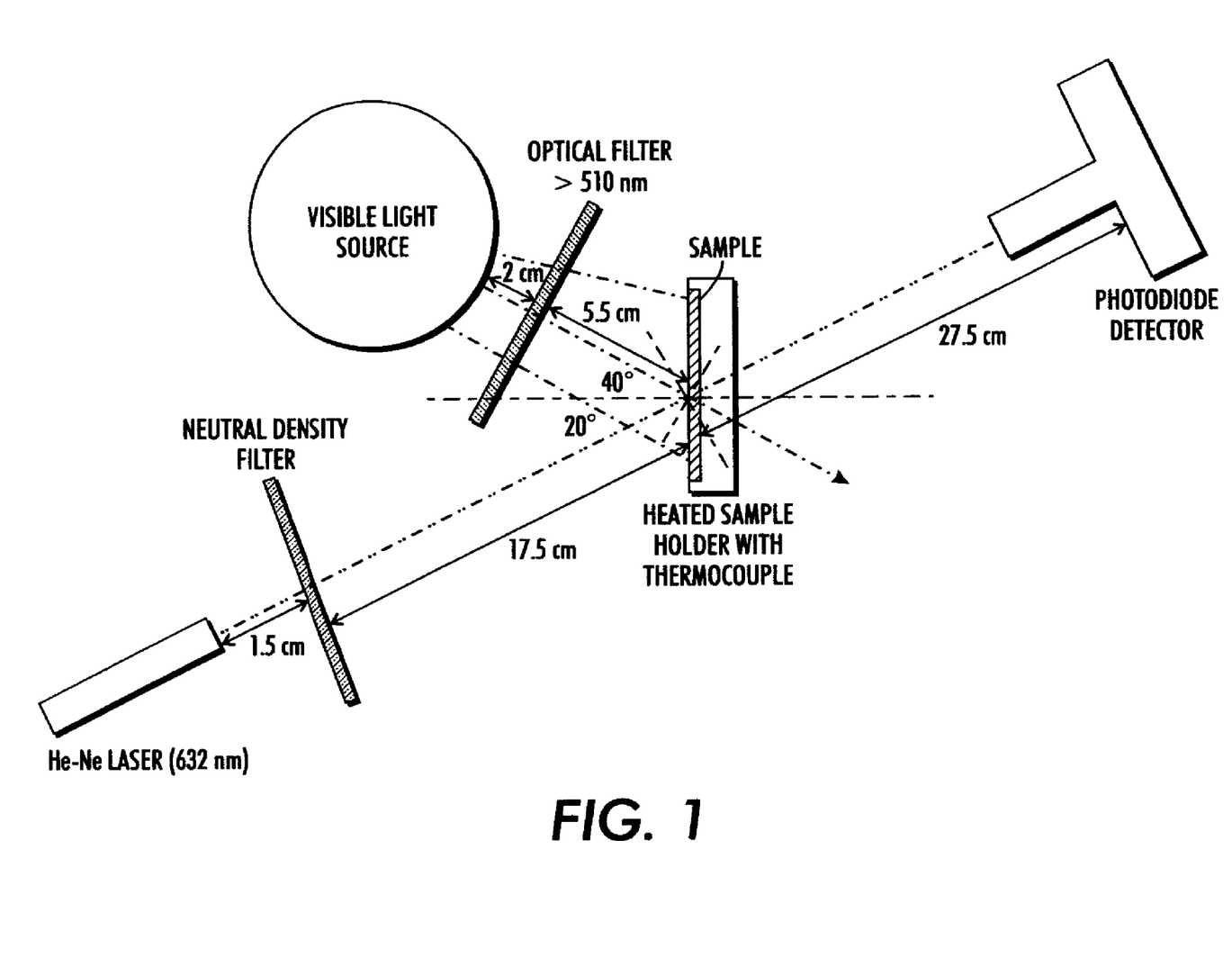
FIG. 1 shows an exemplary testing apparatus for use with the disclosure.
Figure 2A:
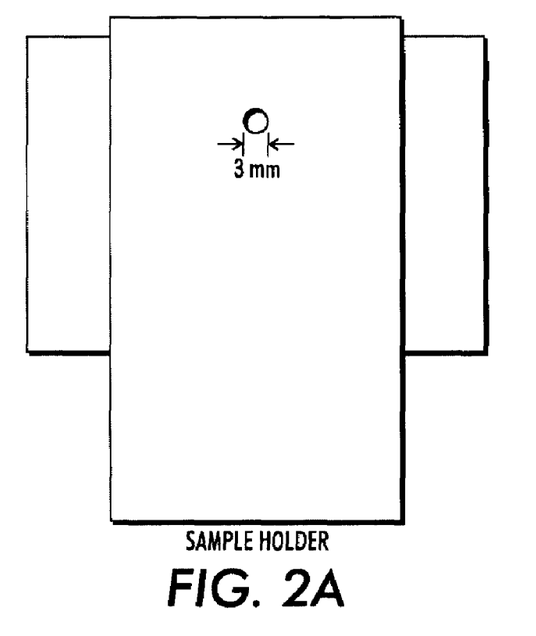
FIGS. 2A and 2B shows additional detail of the heated sample holder of the apparatus of FIG. 1
Figure 2B:
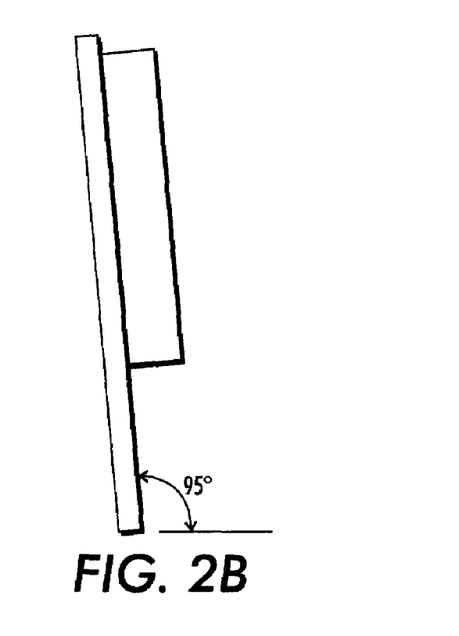

Erasing of the colored photochromes was evaluated as follows, a solution was made by dissolving 70 mg of the photochromic material in 3 ml of a solution of polymethylmethacrylate (PMMA-polymeric binder) dissolved in toluene (PMMA/Toluene=20 g/100 ml). The solution was then spin coated (700 rpm) onto quartz slides (1"×1") for 60 seconds yielding a uniform photochromic film. The quartz slides were then irradiated for 30 s (365 nm; 4 mW/cm$^2$) yielding dark blue films. The quartz slides were then placed in the erasing apparatus at temperature of 140° C. under defined erase conditions as described in FIGS. 1 and 2A and 2B until the films were colorless as determined by a constant laser signal and UV/Vis spectrophotometry.

The printed slides were erased by heating at 140° C. with and without irradiation with visible light. This resulted in a colorless quartz slide with no visible residual color. Next, the slides could be colored again by repeating the write and erase cycle. Table 1 describes the erase half times, defined as the time required to increase the transmitted signal from the laser beam to half of the signal between the initial state (time zero, when sample is colored) and time end (when the signal is constant and highest, i.e. sample is erased completely for erasing of photochromes as described above for examples 2-4.

TABLE 1

Half times (t(50%) for compounds from examples 2-4.

| Example | Heat at 140° C. | Heat at 140° C. with visible light irradiation |
|---|---|---|
| 2 | 360 s | 192 s |
| 3 | 92 s | 68 s |
| 4 | 59 s | 30 s |

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A photochromic material represented by the general formula (I)

[I]

wherein:
each X independently represents hydrogen, an alkyl chain having 1 to 20 carbon atoms, bromine, chlorine or an iodine atom,
A represents a group of formula (a)-(c), and
B represents a group of formula (d)-(f),

[a]

[b]

[c]

[d]

[e]

[f]

wherein:
$R_4$ represents an aryloxy group, a substituted and unsubstituted heteroaromatic group, an alkoxy group, or a substituted alkoxy group, where the alkyl portion of the alkoxy group represents a straight, branched or cyclic, substituted or unsubstituted, alkyl group of from 1 to about 40 carbon atoms, $R_5$ represents an aryl group, a substituted or unsubstituted alkylaryl group wherein hetero atoms either may or may not be present in the alkyl portion of the alkylaryl group or the aryl portion of the alkylaryl group, a cyano group, a carboxylic acid group, or an unsaturated alkene group, $R_6$ represents a hydrogen atom, an alkyl group, a halogen atom, an alkoxy group, a fluoroalkyl group, a cyano group, an aryl group, or a substituted alkylaryl group, $R_7$ represents an alkyl group, an aryl group, an alkylaryl group including substituted alkylaryl groups, unsubstituted alkylaryl groups, and wherein hetero atoms either may or may not be present in the alkyl portion of the alkylaryl group or the aryl portion of the alkylaryl, $R_8$ represents an aryloxy group, substituted and unsubstituted heteroaromatic group, or an alkoxy group or substituted alkoxy group where the alkyl portion of the alkoxy group represents a straight, branched or cyclic, substituted or unsubstituted, alkyl group of from 1 to about 40 carbon atoms,

$R_9$ represents an aryl group, a substituted or unsubstituted alkylaryl groups wherein hetero atoms either may or may not be present in the alkyl portion of the alkylaryl group or the aryl portion of the alkylaryl group, a cyano group, a carboxylic acid group, or an unsaturated alkene group,

$R_{10}$ represents a hydrogen atom, an alkyl group, a halogen atom, an alkoxy group, a fluoroalkyl group, a cyano group, an aryl group, or a substituted alkylaryl group,

$R_{11}$ represents an alkyl group, an aryl group, or a substituted or unsubstituted alkylaryl group wherein hetero atoms either may or may not be present in the alkyl portion of the alkylaryl group or the aryl portion of the alkylaryl, and U and Z each independently represent sulfur or oxygen atoms.

2. A photochromic material represented by the general formulae (II), (III), (IV), (V), (VI), (VII)

[IV]

[VI]

[VII]

wherein:
in formula (II), X represents S or O,
in formula (IV), X represents S, O or C=O, and Y represents O, $CH_2$ or C=O,
in formula (V), Y represents $CH_2$ or C=O,
in formula (VI), X represents CH or N, and
in formula (VII), Y represents $CH_2$ or C=O, and wherein:
A represents a group of formula (a)-(c), and
B represents a group of formula (d)-(f),

[a]

[b]

[c]

[d]

[e]

[f]

wherein:
$R_{b\,4}$ represents an aryloxy group, a substituted and unsubstituted heteroaromatic group, an alkoxy group, or a substituted alkoxy group, where the alkyl portion of the alkoxy group represents a straight, branched or cyclic, substituted or unsubstituted, alkyl group of from 1 to about 40 carbon atoms, $R_5$ represents an aryl group, a substituted or unsubstituted alkylaryl group wherein hetero atoms either may or may not be present in the alkyl portion of the alkylaryl group or the aryl portion of the alkylaryl group, a cyano group, a carboxylic acid group, or an unsaturated alkene group, $R_6$ represents a hydrogen atom, an alkyl group, a halogen atom, an alkoxy group, a fluoroalkyl group, a cyano group, an aryl group, or a substituted alkylaryl group, $R_7$ represents an alkyl group, an aryl group, an alkylaryl group including substituted alkylaryl groups, unsubstituted alkylaryl groups, and wherein hetero atoms either may or may not be present in the alkyl portion of the alkylaryl group or the aryl portion of the alkylaryl, $R_8$ represents an aryloxy group, substituted and unsubstituted heteroaromatic group, or an alkoxy group or substituted alkoxy group where the alkyl portion of the alkoxy group represents a straight, branched or cyclic, substituted or unsubstituted, alkyl group of from 1 to about 40 carbon atoms, $R_9$ represents an aryl group, a substituted or unsubstituted alkylaryl groups wherein hetero atoms either may or may not be present in the alkyl portion of the alkylaryl group or the aryl portion of the alkylaryl group, a cyano group, a carboxylic acid group, or an unsaturated alkene group, $R_{10}$ represents a hydrogen atom, an alkyl group, a halogen atom, an alkoxy group, a fluoroalkyl group, a cyano group, an aryl group, or a substituted alkylaryl group, $R_{11}$ represents an alkyl group, an aryl group, or a substituted or unsubstituted alkylaryl group wherein hetero atoms either may or may not be present in the alkyl portion of the alkylaryl group or the aryl portion of the alkylaryl, and U and Z each independently represent sulfur or oxygen atoms.

3. An image forming medium, comprising
a paper substrate; and
an imaging layer coated on or impregnated into said paper substrate, wherein the imaging layer comprises an imaging composition comprising a photochromic material of claim 1 dissolved or dispersed in a solvent or polymeric binder;
wherein the imaging composition exhibits a reversible transition between a colorless and a colored state.

4. The image forming medium of claim 3, wherein the photochromic material converts from the colorless state to the colored state upon exposure to light of a first wavelength and converts from the colored state to the colorless state upon exposure to at least one of heat and light of a second wavelength different from the first wavelength.

5. The image forming medium of claim 3, wherein the photochromic material readily converts from the colored state to the colorless state only upon exposure to heat at a temperature of from about 80 to about 250° C.

6. The image forming medium of claim 3, wherein the photochromic material does not readily convert from the colored state to the colorless state only upon exposure to heat at a temperature of from about 25 to about 70° C.

7. The image forming medium of claim 3, wherein the imaging composition is applied to the substrate in a layer or as microcapsules.

8. The image forming medium of claim 3, wherein $R_4$ and $R_8$ represents an alkoxy derivative and wherein the alkyl portion of $R_4$ contains 3 or fewer carbon atoms and is selected from methyl, ethyl, propyl or i-propyl and wherein the alkyl portion of $R_8$ contains 4 or more carbon atoms.

9. The image forming medium of claim 3, wherein $R_4$ and $R_8$ represents an alkoxy derivative and wherein the alkyl portion of the alkoxy group of both $R_4$ and $R_8$ contains more than 4 carbon atoms.

10. The image forming medium of claim 3, wherein $R_4$ and $R_8$ represents an alkoxy group and wherein the alkyl portion of the alkoxy group is substituted by one or more groups selected from the group consisting of silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, and sulfonic acid groups.

11. The image forming medium of claim 3, wherein the photochromic material is dispersed in a polymer selected from the group consisting of polyalkylacrylates, polycarbonates, polyethylenes, oxidized polyethylene, polypropylene, polyisobutylene, polystyrenes, poly(styrene)-co-(ethylene), polysulfones, polyethersulfones, polyarylsulfones, polyarylethers, polyolefins, polyacrylates, polyvinyl derivatives, cellulose derivatives, polyurethanes, polyamides, polyimides, polyesters, silicone resins, epoxy resins, polyvinyl alcohol, polyacrylic acid, polystyrene-acrylonitrile, polyethylene-acrylate, vinylidenechloride-vinylchloride, vinylacetate-vinylidene chloride, styrene-alkyd resins, and mixtures thereof.

12. The image forming medium of claim 3, wherein the photochromic material is dissolved in a solvent selected from the group consisting of straight chain aliphatic hydrocarbons, branched chain aliphatic hydrocarbons, halogenated and non-halogenated solvents, such as tetrahydrofuran, trichloro- and tetrachloroethane, dichloromethane, chloroform, monochlorobenzene, toluene, xylenes, acetone, methanol, ethanol, xylenes, benzene, ethyl acetate, dimethylformamide, cyclohexanone, N-methyl acetamide and the like, and mixtures thereof.

13. The image forming medium of claim 3, wherein the photochromic material is present in an amount of from about 0.01% to about 20% by weight of a total weight of the imaging composition.

14. The image forming medium of claim 3, wherein the substrate is selected from the group consisting of plain paper and coated paper.

15. The image forming medium of claim 3, wherein the solvent mixture is provided in the form of encapsulated amounts of the solvent mixture.

16. An image forming medium, comprising
a paper substrate; and
an imaging layer coated on or impregnated into said paper substrate, wherein the imaging layer comprises an imaging composition comprising a photochromic material of claim 2 dissolved or dispersed in a solvent or polymeric binder;
wherein the imaging composition exhibits a reversible transition between a colorless and a colored state.

17. The image forming medium of claim 16, wherein the photochromic material converts from the colorless state to the colored state upon exposure to light of a first wavelength and converts from the colored state to the colorless state upon exposure to at least one of heat and light of a second wavelength different from the first wavelength.

18. The image forming medium of claim 16, wherein the photochromic material readily converts from the colored state to the colorless state only upon exposure to heat at a temperature of from about 80 to about 250° C.

19. The image forming medium of claim 16, wherein the photochromic material does not readily convert from the colored state to the colorless state only upon exposure to heat at a temperature of from about 25 to about 70° C.

20. The image forming medium of claim 16, wherein the imaging composition is applied to the substrate in a layer or as microcapsules.

21. A method of making an image forming medium, comprising applying an imaging layer composition to a paper substrate, wherein the imaging layer composition comprises the photochromic material of claim 1 dissolved or dispersed in a solvent or polymeric binder;
wherein the imaging layer composition exhibits a reversible transition between a colorless and a colored state.

22. The method of claim 21, wherein the applying comprises coating the imaging layer over the paper substrate or impregnating the imaging layer into the paper substrate.

23. A method of forming an image, comprising:
providing an image forming medium comprising:
a paper substrate; and
an imaging layer coated on or impregnated into said paper substrate, wherein the imaging layer comprises an imaging composition comprising the photochromic material of claim 1 dissolved or dispersed in a solvent or polymeric binder,
wherein the imaging composition exhibits a reversible transition between a colorless and a colored state; and
exposing the image forming medium to UV irradiation of a first wavelength in an imagewise manner to form a visible image.

24. The method of claim 23, further comprising:
exposing the image forming medium bearing said image to at least one of heat and light of a second wavelength different from the first wavelength, causing said photochromic material to change from the colored state to the colorless state; and repeating the step of exposing the image forming medium to the UV irradiation of a first wavelength in an imagewise manner at least one additional time.

25. The method of claim 24, wherein the photochromic material readily converts from the colored state to the colorless state only upon exposure to heat at a temperature of from about 80 to about 250° C., and does not readily convert from the colored state to the colorless state only upon exposure to heat at a temperature of from about 25 to about 70° C.

26. The method of claim 23, wherein the exposing is for a time period ranging from about 10 milliseconds to about 5 minutes at an intensity ranging from about 0.1 mW/cm$^2$ to about 100 mW/cm$^2$.

27. An imaging system, comprising:
the image forming medium of claim 3; and
a printer comprising an irradiation source that sensitizes the photochromic material to convert the photochromic material from a colorless state to a colored state.

28. The imaging system of claim 27, further comprising at least one of a second irradiation source being a visible light source in addition to the heating source that converts the photochromic material from a colored state to a colorless state.

* * * * *